US008647614B2

(12) United States Patent
Clineff et al.

(10) Patent No.: US 8,647,614 B2
(45) Date of Patent: Feb. 11, 2014

(54) METHOD FOR STABILIZING VERTEBRAL BODY ARCHITECTURE

(75) Inventors: Theodore D. Clineff, Phoenixville, PA (US); Maarten Persenaire, Phoenixville, PA (US); Gina M. Nagvajara, Narberth, PA (US); Marissa M. Darmoc, Philadelphia, PA (US); Matthew B. Havener, Conshohocken, PA (US); Stephen G. Gilbert, Morrisville, PA (US); Erik M. Erbe, Rancho Santa Fe, CA (US)

(73) Assignee: Orthovita, Inc., Malvern, PA (US)

( * ) Notice: Subject to any disclaimer, the term of this patent is extended or adjusted under 35 U.S.C. 154(b) by 615 days.

(21) Appl. No.: 12/706,530

(22) Filed: Feb. 16, 2010
(Under 37 CFR 1.47)

(65) Prior Publication Data
US 2010/0247478 A1 Sep. 30, 2010

Related U.S. Application Data

(60) Provisional application No. 61/153,487, filed on Feb. 18, 2009.

(51) Int. Cl.
*A61K 31/78* (2006.01)
*A61K 31/74* (2006.01)
*A61P 19/00* (2006.01)
*A61F 2/44* (2006.01)
*A61K 6/08* (2006.01)

(52) U.S. Cl.
USPC .................. 424/78.32; 424/78.08; 424/78.31; 623/17.11; 623/908; 523/116

(58) Field of Classification Search
USPC .............. 424/78.32, 78.08, 78.31; 623/17.11, 623/908; 523/116
See application file for complete search history.

(56) References Cited

U.S. PATENT DOCUMENTS

| 5,681,872 | A | 10/1997 | Erbe |
| 5,914,356 | A | 6/1999 | Erbe |
| 6,800,245 | B1 | 10/2004 | Erbe et al. |
| 2003/0087984 | A1* | 5/2003 | Erbe et al. ..................... 523/113 |
| 2004/0220297 | A1 | 11/2004 | Bonfield et al. |
| 2005/0267577 | A1* | 12/2005 | Trieu ......................... 623/17.11 |
| 2007/0032568 | A1 | 2/2007 | Lin et al. |
| 2009/0012525 | A1 | 1/2009 | Buehlmann et al. |

OTHER PUBLICATIONS

A few minutes: retrieved from internet: http://wiki.answers.com/Q/Discuss:What_is_a_few_minutes. Retrived on Sep. 4, 2012.*

(Continued)

*Primary Examiner* — Ernst Arnold
*Assistant Examiner* — Hong Yu
(74) *Attorney, Agent, or Firm* — Lerner, David, Littenberg, Krumholz & Mentlik, LLP

(57) ABSTRACT

A method for reducing the occurrence of new post-operative fractures in vertebrae of a patient's spine after a vertebroplasty procedure performed to stabilize a fracture in a vertebra of a patient comprising the steps of performing a vertebroplasty procedure to stabilize a fracture in a vertebra of the patient, wherein the vertebroplasty procedure comprises the step of injecting a material into the fractured vertebra, wherein the material is formed by mixing together a first paste and a second paste, wherein the first paste comprises at least one of a polymerizable monomer and a filler, and wherein the second paste comprises at least one of a polymerizable monomer and a filler.

9 Claims, 14 Drawing Sheets

(56) References Cited

OTHER PUBLICATIONS

Erbe et al.: Comparison of a new bisphenol-a-glycidyl dimethacrylate-based cortical bone void filler with polymethyl methacrylate, European Spine Journal, 2001, 10, S147-S152.*
H. Dermond et al, Temperature Elevation Caused by Bone Cement Polymerization during Vertebroplasty, Bone, Aug. 1999; Bone vol. 25, No. 2 Supplement; 17S-21S, Elsevier Science.
S. M. Belkoff, PhD. et al, Biomechanical evaluation of a new bone cement for use in vertebroplasty, Spine, (2000), vol. 25, No. 9; pp. 1061-1064, Lippincott William & Wilkins.
S. M. Belkoff, PhD. et al, The biomechanics of vertebroplasty: The effect of cement volume on mechanical behavior, Spine, Jul. 15, 2001, vol. 26(14);1537-1541, 2000 Lippincott William & Wilkins.
Erik M. Erbe et al, Comparison of a new bisphenol-a-glycidyl dimethacrylate-based cortical bone void filler with polymethyl methacrylate, Eur Spine J., Aug. 24, 2001 10:S147-S152.
P. F. Heini & U. Berlemann, Bone substitutes in vertebroplasty, Eur Spine J., Jun. 14, 2001, 10:S205-S213.
E. M. Erbe et al, Attributes of a novel bone-bonding synthetic cortical bone void filler, Jun. 2001, European Federation of National Associations of Orthopaedics and Traumatology Meeting, Rhodes, Greece, Poster presented.
E. M. Erbe et al, Biomechanical properties of osteoporotic cadaveric vertebral bodies augmented with Cortoss synthetic bone void filler, International Society for the Study of the Lumbar Spine, Jun. 2001, Edinburgh, Scottland, Poster presented.
T. D. Clineff et al, Quantitative evaluation of bone apposition to Cortoss at 1 year, Orthopaedic Research Society, Feb. 2001, San Francisco, CA, Poster presented.
Erbe, E. M., et al., Cortoplasty—Augmentation of Osteoporotic Vertebral Compression Fractures with Cortoss, Annual Meeting of Society for Biomaterials, Apr. 18-21, 2007.
Gheduzzi, S. et al, Mechanical characterization of three precutaneous vertebroplasty biomaterials. J. Mater Sci, Mater Med. 2006; 17:421-426.
Homminga, J. et al., Osteoporosis changes the amount of vertebral trabecular bone at risk for fracture but not the vertebral load distribution. Spine. 2001; 26 (14): 1555-1561.
Kim, MJ, et al, Vertebroplasty versus kyphoplasty: biomechanical behavior under repetitive loading conditions. Spine. 2006; 31(18): 2079-2084.
Lou, J., et al. Mechanical efficacy of vertebroplasty: influence of cement type, BMD, Fracture Severity, and disc degeneration. Bone. 2006, DOI: 10.1016/j.bone.2006.11.021.
Molly S, Mathis, J. Belkoff, S.M. The effect of vertebral body percentage fill on mechanical behavior during percutaneous vertebroplasty. Spine. 2003; 28(14): 1549-1554.
Jasper, Deramond, et al. Material properties of various cements for use with vertebroplasty. Journal of Material Sci: Mater. Med., 2002, 13, 1-5.
Lewis, G. Injectable bone cements for use in vertebroplasty and kyphoplasty: State of the art review. Wiley Interscience (www.interscience.wiley.com) 2005; DOI: 10.1002/jbm.b.30398.
Pomrink et al., Evaluation of the reaction kinetics of Cortoss, a thermoset cortical bone void filler. Biomaterials 2003, 1023-1031.
Cohen, JE. et al. Percutaneous vertebroplasty: Techinque and results in 192 procedures. Neurol Res. 2004; 26: 41-49.

Jensen, ME, et al. Position statement on percutaneous vertebral augmentation: a consensus statement developed by the American Society of interventional and therapeutic neuroradiology, society of interventional radiology, Amercian Association of Neuological Surgeons/Congress of Neuological Surgeons, and American Society of Spine Radiology. AM J. Neuroradioi. 2007; 28: 1439-1443.
Mehbod, Aunoble, Le Huec, Vertebroplasty for osteoporotic spine fracture: prevention and treatment. European Spine Journal, 2003, 12, S155-S162.
Riggs, BL, Melton, LJ., The worldwide problem of osteoporosis: insights afforded by epidemiology. Bone. 1995; 17:505S-511S.
Shen, M, Kim Y. Osteoporotic vertebral compression fractures: a review of current surgical management techniques. Am. J. Orthop 2007; 36(5): 241-248.
Voormolen, MHJ, et al. Percutaneous Vertebroplasty compared with optimal pain medication treatment: Short-Term Clinical outcome of patients with subacute or chronic painful osteoporotic vertebral compression fractures. The VERTOS Study, Am. J. Neuroadiol. 2007; 28:555-560.
Bae, H. et al. Characteristics and clinical experience using a novel bioceramic for treating vertebral compression fractures in vertebroplasty and kyphoplasty: report on the first 40 patients. Proceeding of the NASS 20th annual meeting/ The Spine Joural. 2005, 5:1S-189S.
Beric, V. Ultra-low volume vertebroplasty using Cortoss bone substitute. Scientific Paper (Oral presentation) American Society of Neuroadiology. 2006.
Pradhan, B, Bae, HW. Prospective randomized vertebroplasty trial at a single institution: Cortoss compared to PMMA. Poster Presentation; Congress of Neurological Surgeons. 2007.
Palussiere, J. et al. Clinical results of an open prospective study of a bis-GMA composite in percutaneous vertebral augmentation. Eur. Spine J. 2005; 14:982-991.
Berlemann, U. et al. Adjacent vertebral fracture after vertebroplasty: a biomechanical investigation. The Journal of Bone & Joint Surgery (Br). 2002; 84-B(5): 748-752.
Fribourg, D. et al. Incidence of subsequent vertebral fracture after kyphoplasty, Spine. 2004; 29 (20): 2270-2276.
Lin, E. P., et al. Vertebroplasty: cement leakage into the disc increases the risk of new fracture of adjacent vertebral body. American Journal of Neuroradiology. 2004; 25: 175-180.
Syed, M. I. et al. Intradiskal Extravasation with low-volume cement filing in percutaneous vertebroplasty. American Journal of Neuroradiology. 2005; 26: 2397-2401.
Trout, A.T. et al. New fractures after vertebroplasty: adjacent fractures occur significantly sooner. American Journal of Neuroradiology. 2006; 27: 217-223.
Liebschner, M.A., et al. Effects of bone cement volume and distribution on vertebral stiffness after vertebroplasty, Spine. 2001; 16(14): 1547-1554.
Lindsay R, Silverman SL, et al. Risk of new vertebral fracture in the year following a fracture, JAMA, 2001, 285: 320-323.
Voormolen MHJ, Lohle PNM, et al. The risk of new osteoporotic vertebral compression fractures in the year after percutaneous vertebroplasty, J Vasc Interv Radiol, 2006, 17: 71-76.
International Search Report for PCT/US2010/024476 dated Apr. 19, 2010.
Australian Office Acion for Application No. 2010216124 dated Aug. 9, 2013.

* cited by examiner

METHOD FOR STABILIZING VERTEBRAL BODY ARCHITECTURE

CROSS-REFERENCE TO RELATED APPLICATIONS

This application claims priority to U.S. Provisional Application No. 61/153,487 filed Feb. 18, 2009.

TECHNICAL FIELD

The present invention relates generally to sterile, polymerizable, biocompatible compositions for injection into bone which will polymerize and restore the bone's biomechanical properties. In particular, the present invention relates to the use of such compositions in vertebroplasty procedures to reduce the occurrence of new post-operative fractures in vertebrae of a patient's spine after a vertebroplasty procedure is performed. The present invention also relates to the use of such compositions in vertebroplasty procedures to reduce pain in the months subsequent to the procedure and to stabilize the remaining vertebral architecture.

BACKGROUND

Osteoporosis, the progressive loss of bone tissue, affects more than 30 million Americans. Normal bone is composed of a framework made of a particular protein, collagen, and calcium salts. Osteoporosis depletes both the collagen and the calcium salts from the bone. The bone then becomes weaker and more prone to breaks (fractures), either by cracking or by collapsing (compression).

Patients with osteoporosis generally have no symptoms until bone fractures begin. Fractures of the vertebrae of the spine are usually a result of minor compression forces on bone. This leads to collapse of the vertebrae. A fracture that collapses a vertebra in this way is referred to as a vertebral compression fracture.

Spinal vertebral fractures can occur without pain. However, they often cause a severe "band-like" pain that radiates from the spine around both sides of the body. Spinal fractures cause a loss of height of the spine resulting in the person becoming shorter. A change in curvature of the spine can also occur giving the individual a hunched-back appearance (the so-called dowager's hump). This can contribute to chronic backaches.

In the past, the treatment of vertebral compression fractures has been limited to taking pain medicine, resting, avoiding injury, and bracing. More recently surgical therapies have become available for the treatment of these fractures.

Vertebroplasty is a minimally invasive procedure to treat vertebral compression fractures that is typically performed by a radiologist or orthopedic surgeon. Vertebroplasty involves injecting a cement-like material into the collapsed vertebra in order to stabilize and strengthen the crushed bone. The cement is typically inserted with a needle, catheter and/or syringe through anesthetized skin into the body of the vertebra under the guidance of specialized x-ray equipment. Once inserted, the material soon hardens, forming a cast-like structure with the locally broken bone. The advantages of vertebroplasty, aside from prompt pain relief, include better mobility.

The physio-chemical properties and fill patterns of the cement commonly employed in vertebroplasty, polymethylmethacrylate (PMMA), have been widely thought to introduce secondary bone damage and cause failure of other vertebrae—either adjacent to the "cemented" vertebra or remote vertebrae (i.e., vertebrae at least two positions removed from the "cemented" vertebra). For example, referring to FIGS. 1 and 1a, traditional PMMA bone cement materials tend to have a localized or compact distribution within the vertebra. Such compact distribution has been shown to cause stress concentrations in the bone tissue directly above and below the PMMA, which may lead to fractures of the adjacent and remote vertebrae. The stress concentrations in the bone tissue directly above and below the PMMA may also cause microfractures leading to occurrences of pain. Furthermore, the localized distribution or "bolus" of material typically requires large volumes of material to be injected which can lead to increased patient exposure to implant material.

Accordingly, there is a need in the art for a vertebroplasty method that employs a material that does not suffer from the above drawbacks. The present invention fulfills this need by employing methods that utilize materials that can flow and interdigitate into the vertebral body, in small volumes.

SUMMARY

The present invention is directed to methods for reducing the risk of fractures in a patient's adjacent vertebrae after a vertebroplasty procedure is performed to stabilize a fracture in a vertebra of a patient. The present invention is also directed to methods for reducing the occurrence of pain in a patient after a vertebroplasty procedure and for alleviating pain after a vertebroplasty procedure is performed.

The methods of the present invention utilize materials capable of flowing throughout, interdigitating with, and bonding to the native trabecular bone of the vertebral body. The materials of the present invention disperse more readily than traditional PMMA materials, thereby allowing small volumes of material to be injected while achieving the same, or better, stability/pain relief/occurrence of adjacent level fractures than PMMA materials.

BRIEF DESCRIPTION OF SEVERAL VIEWS OF THE DRAWINGS

The invention is best understood from the following detailed description when read in connection with the accompanying figures. It is emphasized that, according to common practice, the various features of the figures are not to scale. On the contrary, the dimensions of the various features are arbitrarily expanded or reduced for clarity. Included are the following figures:

FIG. 5 is a low magnification image showing the material in the defect site within the vertebral body. FIG. 5a is a higher magnification image of the same specimen showing direct bone apposition between the cancellous bone and the material.

FIG. 6 is a low magnification image showing the defect site in the vertebral body. Note that the site appears empty because the PMMA dissolves during tissue processing. FIG. 6a is a higher magnification image of the same specimen showing a thin fibrous membrane between empty space previously occupied by the PMMA and adjacent bone.

FIG. 7 shows the present invention material in the vertebral body defect site with bone growth over the defect site. FIG. 7a is a higher magnification image of a separate specimen showing the interdigitation-flowing of material into native bone, of the present invention material.

FIG. 8 shows the site that contained PMMA material with tissue ingrowth into probable voids around the edges of the injected PMMA. FIG. 8a is a higher magnification image of a separate specimen showing a very thin fibrous membrane between the space occupied by the PMMA and the adjacent bone.

DETAILED DESCRIPTION OF ILLUSTRATIVE EMBODIMENTS

Figure 1:
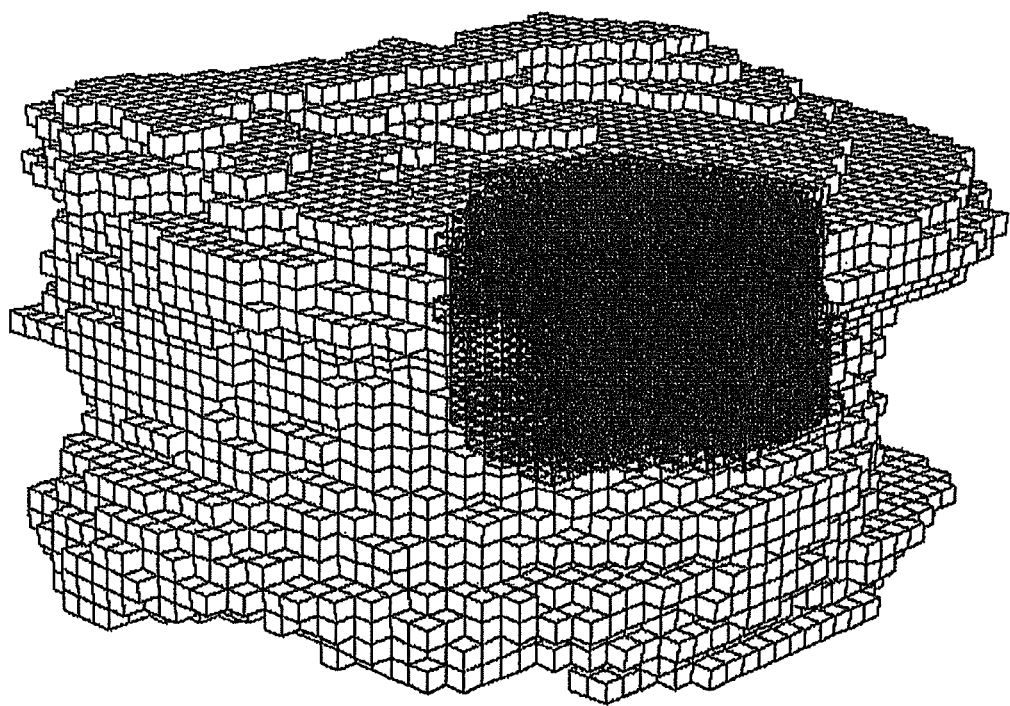
FIG. 1 is an image generated from pixel values from a post-operative quantitative computed tomography (QCT) scan that illustrates the compact fill pattern observed with traditional PMMA bone cement materials.
Figure 1A:
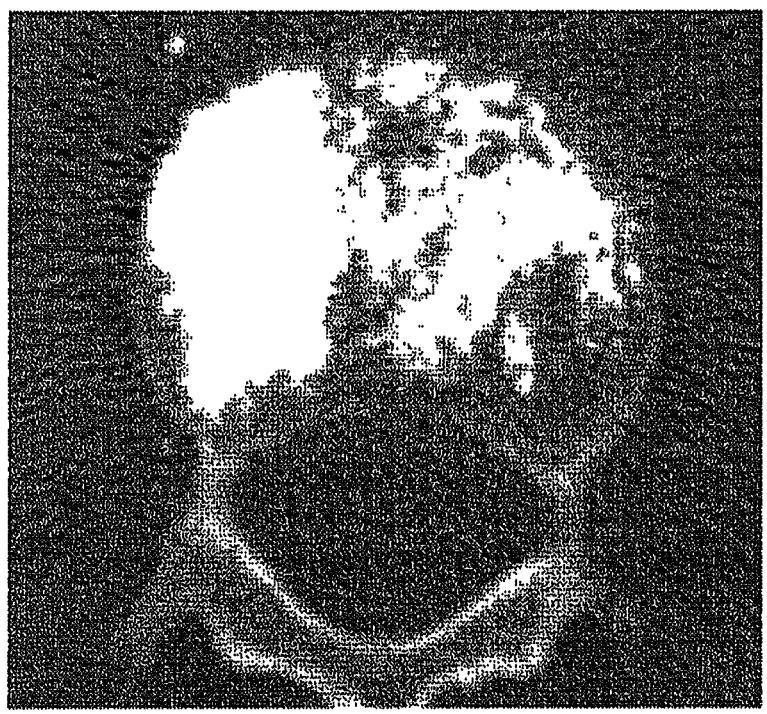
FIG. 1a is a post-operative image from a patient showing the bolus fill pattern inside the vertebral body after injection with a traditional PMMA bone cement material.
Figure 2:
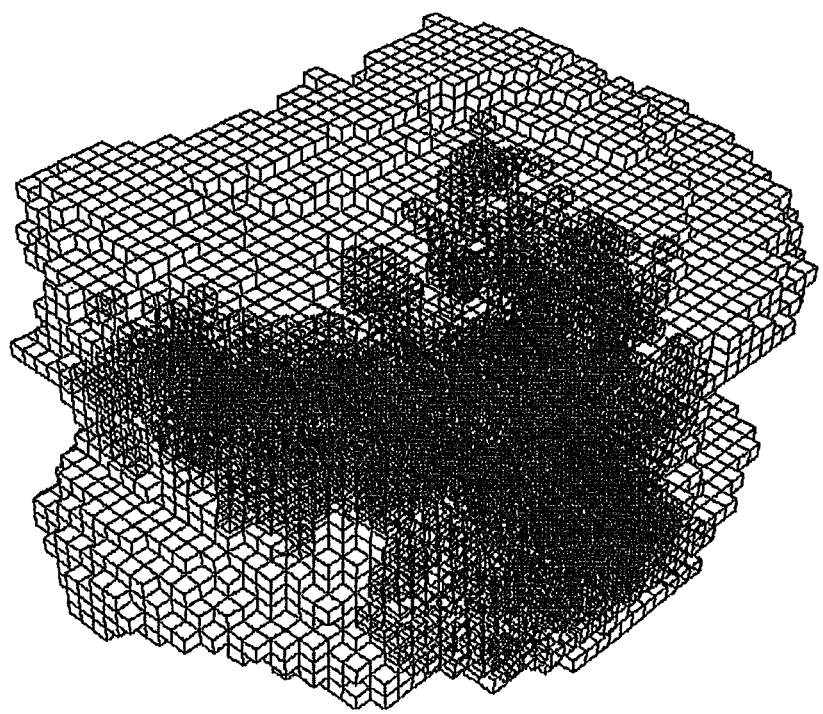
FIG. 2 is an image generated from pixel values from a post-operative QCT scan that illustrates a dispersed fill pattern observed with the material employed in the present invention.
Figure 2A:
FIG. 2a is a post-operative image from a patient showing the dispersed fill pattern inside the vertebral body after injection with the present invention material.

The present invention is directed to materials for use in vertebroplasty procedures and to methods for utilizing these materials to reduce the risk of fractures in a patient's adjacent vertebrae after a vertebroplasty procedure is performed to stabilize a fracture in a vertebra of a patient. The present invention is also directed to methods for reducing the likelihood of occurrence of pain in a patient after a vertebroplasty procedure and for alleviating pain after a vertebroplasty procedure is performed. The preferred materials utilized in the present invention include materials capable of flowing throughout and interdigitating with the native trabecular bone of the vertebral body. FIG. 2 is an image generated from pixel values from a post-operative QCT scan that illustrates a dispersed fill pattern observed with the material employed in the present invention; and FIG. 2a is a post-operative image from a patient after injection with the material employed with the present invention. By flowing and interdigitating into the native bone, the materials of the present invention are capable of stabilizing a patient's vertebral body upon injection of small amounts of material. The materials of the present invention are capable of bonding to bone with minimal fibrous tissue between the material and the native or host bone. This material characteristic further enhances the stability of the native bone construct upon injection of the material into a patient's bone. The materials of the present invention are more hydrophilic than traditional PMMA materials, thereby coating the trabeculae or struts of the native bone, and are capable of immediate load-bearing.

In one embodiment, the present invention provides a method for reducing the risk of fractures in a patient's adjacent vertebrae after a vertebroplasty procedure is performed to stabilize a fracture in a vertebra of the patient, the method comprising the steps of: performing a vertebroplasty procedure to stabilize a fracture in a vertebra of the patient, wherein the vertebroplasty procedure comprises the step of injecting a material into the fractured vertebra, wherein the material is formed by mixing together a first paste and a second paste, wherein the first paste comprises at least one of a polymerizable monomer and a filler, and wherein the second paste comprises at least one of a polymerizable monomer and a filler.

As defined herein, the phrase "injecting a material" refers to the injection of a bone cement, bone augmentation material or other such material that can be injected into the vertebral body as described herein. In certain embodiments, the material injected can polymerize or transition from a first liquid and powder state, or from a paste-like state to a second hardened state. The time it takes for the material to reach the hardened state upon commencement of mixing the liquid with the powder, or mixing multiple pastes together is referred to as the material's set-time. Prior to hardening, the material may be manipulated. This time frame is referred to as the material's working time.

In certain embodiments, the present invention provides a method for reducing the occurrence of pain in a patient after a vertebroplasty procedure to stabilize a fracture in a vertebra of the patient, the method comprising the steps of: performing a vertebroplasty procedure to stabilize a fracture in a vertebra of the patient, wherein the vertebroplasty procedure comprises the step of injecting a material into the fractured vertebra, wherein the material is formed by mixing together a first paste and a second paste, wherein the first paste comprises at least one of a polymerizable monomer and a filler, and wherein the second paste comprises at least one of a polymerizable monomer and a filler.

In yet another embodiment, the present invention provides a method for both reducing the risk of fractures in a patient's adjacent vertebrae and alleviating pain after a vertebroplasty procedure is performed to stabilize a fracture in a vertebra of the patient, the method comprising the steps of: injecting a material into the fractured vertebra in an amount less than 3 cc, and allowing the material to harden for a period of 2.0-8.0 minutes or more preferably 2.0-4.0 minutes to obtain heightened pain relief at about 3 months after the step of performing the vertebroplasty procedure; wherein the material is formed by mixing together a first paste and a second paste, wherein the first paste comprises at least one of a polymerizable monomer and a filler, and wherein the second paste comprises at least one of a polymerizable monomer and a filler. In most instances, the amount of material injected is less than 3 cc in the lumbar vertebral bodies and less than 2.5 cc in the thoracic vertebral bodies.

As defined herein, heightened pain relief is defined by a significant reduction in pain as measured by the Visual Analog Scale (VAS) in comparison to traditional PMMA bone cement compositions.

The method of the present invention employs compositions comprising one or more polymerizable monomers and one or more fillers. In certain embodiments, these compositions are viscous liquids or pastes. The viscosity of these pastes ranges from about 40,000 centipoise (cP) to about 400,000 centipoise, as measured, for example, via a Brookfield viscometer. In other embodiments, in which the pastes are mixed and delivered using a syringe, the viscosity of the mixed composition as measured via extrusion force may range from about 100,000 to 300,000 cP.

Relatively low viscosity, syringable pastes are best suited for the filling of bony defects, fracture repair, and implant fixation and revision. The compositions employed in the method described herein are ideally suited to enable small amounts of material to be injected. That is, due to the material properties, flow characteristics and viscosity of the materials described herein, smaller volumes of material may be used to achieve stabilization of the same vertebral body volume that would otherwise be treated with large volumes of traditional PMMA bone cement materials. For instance, in the present invention method, the average volume of material injected may range from 1 cc-5 cc, or more preferably 1 cc-3.5 cc, in comparison to 3 cc-10 cc for traditional PMMA materials. Although leakage rates may not be reduced in comparison to PMMA compositions utilized for vertebral augmentation, the actual amount or volume of material which leaks is typically reduced when the compositions described herein are used in the method of the present invention. For instance, the average leak volume of a composition of the present invention used in the disclosed method may be 0.14 cc in comparison to 0.2 cc for traditional PMMA compositions (significance of p<0.05). This results in less material exposure to the patient especially when multiple vertebral bodies within a single patient are treated. It should be realized that it is not only the lower injection and lower leakage volumes that allows for multiple vertebral bodies (e.g., >3 vertebral bodies) within a single patient to be treated but also the chemistry of the composition of the present invention and its inherent lower volatile monomer content.

Syringable pastes, such as the material described herein, flow to fill voids, and crevices, and adhere tightly to the surface of the bone, tissue, or implant. Flowability can be important for tight adherence and removal of micromotion when implant securing is being achieved. The lack of implant motion can reduce inflammation and determine the success of the implant system over time. Materials used in the present invention method produce less fibrous tissue encapsulation therefore less micromotion of bone fragments. Another added benefit of the flowability of the material described herein (e.g., the low pressure low viscosity material characteristics) is a decreased incidence of material flowback during or after injection, and therefore less extravascular epidural leaks.

The polymerizable monomer or monomers (or dimers or trimers) that comprise the viscous, paste compositions employed by the present invention are preferably ethylenically unsaturated monomers, and more preferably comprise an acrylate functional group. The term "monomers", as used herein, can also represent dimers, trimers, resins, resin components, or any other polymerizable component. Examples of the monomers include, but are not limited to, bisphenol-A-glycidyl dimethacrylate (bis-GMA), triethylene glycol dimethacrylate (TEGDMA), or bisphenol-A-ethoxy dimethacrylate (bis-EMA). In preferred embodiments, the monomers may be activated, for example, by the addition of benzoyl peroxide (BPO) or other free radical formers and tertiary amines, or other reducing agents, such as but not limited to dihydroxyethyl-para-toluidine (DHEPT), DMAPE, DMEPT, ascorbic acid, that may provide an electron withdrawing group that initiates free radical polymerization.

The pastes of the present invention may further comprise, but are not limited to, polymerization inhibitors, polymerization activators, polymerization initiators, radiopacifiers, reinforcing components (i.e., fibers, particles, micro spheres, flakes, etc.), bioactive fillers, neutralizing resins, diluting resins, antibiotic agents, coloring agents, plasticizers, coupling agents, free radical generators, radiographic contrast agents, and antibiotics. The pastes of the present invention may also comprise trace elements of strontium, magnesium, lithium and similar elements found in bone.

Polymerization inhibitors may be added to the composition to minimize polymerization during storage. Examples of polymerization inhibitors include hydroquinone, and various functional equivalents such as butylhydroxytoluene (BHT), 2-hydroxy-4-methoxy-benzophenone (UV-9), methyl ether hydroquinone (MEHQ), 4-benzyloxy phenol and 3,5-diisopropyl phenol.

Polymerization activators are typically amines and are used to promote free radical generation from organic peroxide initiators in addition polymerizations. The free radicals are generated at temperatures around room temperature or below by chemical reduction of the peroxide. Examples of such activators are, N,N-dimethyl-p-toluidine (DMEPT), dihydroxyethyl-para-toluidine (DHEPT), and functional equivalents such as N,N-deimethyl-meta-toluidine, N,N-dimethyl-ortho-toluidine, and N-ethyl-N-hydroxyethyl-meta-toluidine.

Color agents may be added to the composition to impart color and may include dyes, paint pigments, or reduced metal particles.

Plasticizers may be added to the composition to facilitate processing and increase the flexibility of the final product. Examples of plasticizers include TEGDMA, HEMA and phthalates such as diethyl phthalate, benzylbutyl phthalate, dibutyl phthalate, and dibenzyl phthalate.

Coupling agents are used to link the filler within the composition to the polymer matrix. Typical coupling agents include silanes such as γ-methyacryloxypropyltrimethoxysilane or other cationic coupling agents.

Free radical generators are substances within the composition that decompose to form free radicals that begin the process of polymerization in addition reactions. Examples of free radical generators include benzoyl peroxide, tent-butyl peroxide, and diethyl peroxide.

Radiographic or diagnostic contrast agents may be added to the composition to enable the composition to be discerned upon x-ray or other diagnostic means. Examples of such agents include barium boroaluminosilicate glasses and glass-ceramics, barium sulfate ($BaSO_4$), zirconium dioxide ($ZrO_2$), chromium oxide (CrO), Ta, Gd or other heavy metal particulate, or bismuthic compounds such as $Bi_2O_3$ and $Bi(OH)_3$.

In preferred embodiments, the polymerizable systems are comprised of two pastes designated as pastes A and B. In certain preferred embodiments, paste A is comprised of at least one or more fillers and at least one or more resins. Exemplary resin components contained within paste A may include from about 0 to about 25% by weight bisphenol-A glycidyl dimethacrylate (bis-GMA), from about 0 to about 18% by weight triethylene glycol dimethacrylate (TEGDMA), and from about 0 to about 0.009% by weight butylhydroxytoluene (BHT). In certain preferred embodiments, paste B is also comprised of at least one or more fillers and at least one or more resins. Exemplary resin components contained within paste B may include from about 0 to about 15% by weight bisphenol-A glycidyl dimethacrylate (bis-GMA), from about 0 to about 15% by weight triethylene glycol dimethacrylate (TEGDMA), from about 0 to about 15% by weight bisphenol-A-ethoxy dimethacrylate (bis-EMA), from about 0-0.07% by weight butylhydroxytoluene (BHT), and from about 0 to about 0.70% by weight of BPO.

Various combinations of the amine:BPO:BHT additives within the paste will yield specific working and set-times. Each set character will depend on the mass of material used, energy imparted upon mixing, and the temperature of the body (normally 37° C.) at the implant site. In certain preferred embodiments, the material has a set-time from about 2.0 minutes to about 8.0 minutes. In some embodiments, the material will undergo a "snap-set" rather than transition through a dough state prior to hardening.

The monomers and other additives are blended together to form one or more paste composition precursors. The duration of the blending operation will vary depending upon the constituents that comprise the paste composition precursors. In preferred embodiments, the blending of the monomers and other additives within the paste composition precursors activates the polymerization of the composition.

As mentioned previously, the viscous paste or pastes further comprise one or more fillers. Fillers, which may be inorganic or organic compounds, but preferably are inorganic compounds, are added to the paste to enhance, inter alia, the mechanical or the rheological properties of the paste composition. Examples of suitable fillers include, but are not limited to, barium glass, barium-boroaluminosilicate glass ($BaO-B_2O_3-Al_2O_3-SiO_2$), silica ($SiO_2$), 45S5 glass, bioactive glass, ceramics, glass-ceramics, bioactive synthetic Combeite glass-ceramic ($Na_2O-CaO-P_2O_5-SiO_2$) or combinations thereof. These fillers may possess a variety of morphologies such as, but not limited to, needles, particulate, flakes, cylinders, long fibers, whiskers, or spherical particles. In preferred embodiments, the filler is comprised of particles with an average particle size ranging from less than about 1.0 µm up to a range of from 2 to 3 millimeters (mm). Preferably, the average particle size distribution ranges from 1 to 100 µm. The particles may be of a single size within the above noted range or may be bimodal (of two different particle sizes within the range), trimodal, etc.

Optionally, the filler or fillers may be pre-dried and screened prior to sterilization as needed. In preferred embodiments, one or more fillers are coated with silane which acts as a coupling agent prior to sterilization.

In a presently preferred embodiment, paste composition A comprises a silane-coated, glass-ceramic filler that is combined in a blending step with a silane-coated silica to form filler A. An example of a silane-coated, glass-ceramic filler is one manufactured by Mo-Sci, Corp. of Rolla, Mo. The glass filler may, optionally, be pre-dried and screened prior to dry-heat sterilization or, alternatively, gamma-sterilized. Paste composition B comprises a silane-coated barium glass, such as, for example, the barium-boroaluminosilicate glass manufactured by Sci-Pharm, Inc. of Pomona, Calif. in addition to silane-coated silica.

In preferred embodiments, the filler level of pastes A and B can vary from 65 to 85% by weight total filler content and includes the preferred bioactive glass-ceramic, such as the Combeite glass-ceramic ("CGC") filler and composition disclosed in U.S. Pat. No. 5,681,872, and assigned to Orthovita, Inc., the assignee of the present invention. U.S. Pat. No. 5,681,872 is incorporated herein in its entirety by reference. The content of the preferred bioactive glass-ceramic preferably ranges from about 10 to about 99% by weight of that filler. It is preferred that the particle size distribution of the fillers be broad, bimodal, or preferably trimodal, also of which being less than about 300 micrometers, even more preferably less than 50 µm, with less than about 5% by weight being sub 0.1 microns in size.

Preferably, the filler and monomer are subjected to a sterilization procedure that exposes such components under suitable conditions to a sterilizing agent such as, for example, dry heat, gamma, E-beam, membrane filtration or ethylene oxide (EtO).

After the filler and monomer are sterilized, the filler and the monomer are combined to form one or more paste compositions. In preferred embodiments, the paste composition precursor comprising the monomer and filler are combined to form one or more pastes in an aseptic process, i.e., using equipment that has been pre-sterilized and combining the components of the paste compositions in a class 100 or greater clean room. Depending upon the components of the paste composition, a vacuum that ranges from 0 to 29.5 in Hg may be pulled to minimize macro-sized air bubbles. For example, in certain presently preferred embodiments, the A paste composition that will fill the A-side cartridge has an applied vacuum of 20 in Hg pulled whereas the B paste composition that will fill the B-side cartridge has an applied vacuum of 5 in Hg. The equipment used to blend the monomer, filler, or other constituents to form the paste compositions, such as the mixing equipment, spatulas, blades etc., are preferably pre-sterilized using steam or autoclave sterilization.

The paste is preferably contained within a primary packaging that comprises one or more cartridges, caps, O-ring pistons, and external pouches. Each of the primary packaging components is sterilized prior to the aseptic filling of the paste or pastes. In preferred embodiments, the primary packaging components are sterilized via gamma sterilization or other sterilization techniques such as EtO, or E-beam sterilization.

One or more pastes are aseptically filled into cartridges that further comprise a cap and an O-ring piston. In preferred embodiments, paste compositions A and B are loaded into a monolithic, double-chambered cartridge such as the double-chambered cartridge that is manufactured by Medmix Systems AG of Rotkreuz, Switzerland. Preferably, the double-chambered cartridge has two chambers that keep the pastes separated from each other. Further embodiments of the present invention may include, but are not limited to, multiple-chambered, i.e., triple- or quadruple-chambered cartridges for three or four paste compositions. The cartridge preferably has a dispensing nozzle and cap to seal the contents prior to use.

Filling the cartridges, assembling the piston into the cartridge, encapsulating the cartridges into one or more pouches and then thermo-sealing the cartridges, is typically conducted within an isolated system or isolator. The isolator preferably employs vaporous hydrogen peroxide (VHP) to obtain a sterile environment or SAL of from about $10^{-6}$ to about $10^{-5}$;

however, other methods of rendering the area sterile may be used without departing from the spirit of the invention. In some embodiments, the paste is aseptically filled into the cartridge using filling equipment which is selected to minimize the risk of contamination of the sterile material. Preferably, non-product contact filling equipment such as the Trideck filler manufactured by Trideck, Inc. of Brookfield, Conn. is used. Depending upon the composition of the paste or pastes, the filling may further be conducted under hot or cold temperatures (hot filled or cold filled) or conducted under vacuum. After the cartridge or chambers of the cartridge are filled, the O-ring piston assembly is assembled into the cartridge to form an air-tight seal. In other embodiments, the piston assembly is first inserted into each individual chamber of the cartridge and then the paste is aseptically front-filled into the cartridge. The filled cartridge and piston may then be packaged within an external pouch. In preferred embodiments, the filled cartridges and piston assemblies are packaged within a dual pouch arrangement, or an inner and outer pouch. Examples of the external packaging for the filled cartridges my comprise a Tyvek®/polyester pouch manufactured by Tolas Healthcare Packaging of Feasterville, Pa. and/or polyvinyl pouch. Still other external packages may include, but not be limited to, foil pouches, opaque pouches for light sensitive materials, or other permeable pouches. The cartridges are then thermally sealed. In certain preferred embodiments, the cartridge is inserted into an internal polyvinyl pouch which is then placed within a TYVEK®/polyester pouch. Both internal and external packages are thermally sealed simultaneously.

The filled cartridges may be packaged along with accessories for the presently preferred embodiment of the present invention. These accessories are individually sterilized and packaged into a single-use kit. This kit may comprise a delivery gun and one or more tips, or "mix-tips" of various sizes and configurations. In preferred embodiments, a single-use delivery gun, such as the gun manufactured by Medmix Systems AG of Rotkreuz, Switzerland, may be used that accommodates a dual-chambered cartridge that contains two different paste compositions. Still further accessories to the kit of the present invention include the straight, tapered, and Leur-lock mix-tip of the present invention. In preferred embodiments, these mix-tips are also manufactured by Medmix Systems AG of Rotkreuz, Switzerland, and are sized to fit the nozzle end of the cartridge. The mix-tip has mixing elements contained therein that allow the paste compositions in the separate chambers to mix and delivery a substantially homogeneous blend. Other components to the systems of the present invention may include a micro delivery system. All of the components are pre-sterilized and packaged prior to use. In preferred embodiments, the components are sterilized via gamma sterilization. After the components are sterilized, the components are placed into an external package to ensure sterility. An example of this external package may include a TYVEK®/polyester pouch manufactured by Tolas Healthcare Packaging of Feasterville, Pa. The present invention may further include additional kits that comprise refills of the paste compositions, preferably in cartridge form, and mix-tips.

In certain preferred embodiments, the end-user opens the external and internal pouches that house the dual-chambered cartridge and loads the cartridge into the delivery gun within a sterile environment, such as a surgical operating room. The plunger of the gun uniformly engages the pistons within each chamber to dispense the pastes. The individual caps covering the outlets on each chamber of the cartridge are removed and the mix-tip is installed. The mix-tip is preferably shaped to allow the pastes to flow through their respective outlets on each chamber and ultimately to flow through one central orifice into a mixing element. The mix-tip further has an mixing element that is shaped like an auger to combine the pastes into a homogeneous blend prior to dispensing. For best results, the first inch of the blend is discarded to insure uniform mixing of both pastes. The cement material is then ready to be used.

In a typical vertebroplasty procedure, the patient is treated with local anesthesia and light sedation, usually in an x-ray suite or operating room on an outpatient basis. A needle is guided into the fractured vertebra under x-ray guidance through a small puncture in the patient's skin. The cement according to the present invention is injected into the fractured vertebra via the use of a catheter, tubing and/or syringe, filling the spaces within the bone—with the goal of creating a type of internal cast (a cast within the vertebra) to stabilize the vertebral bone. The catheter and/or syringe is removed and the cement hardens quickly (i.e., in from about 2.0 to 8.0 minutes, or more preferably from about 2.0 to 4.0 minutes), congealing the fragments of the fractured vertebra and stabilizing the bone. The needle is removed once the vertebral body has been stabilized.

Additional objects, advantages, and novel features of this invention will become apparent to those skilled in the art upon examination of the following examples of the invention. The examples are included to more clearly demonstrate the overall nature of the invention and, thus, are illustrative and not restrictive of the invention.

EXAMPLES

Example

Hydrophilicity of Present Invention Material

Testing was conducted to evaluate the wettability of one exemplary material employed with the present invention (sold under the tradename Cortoss™ Bone Augmentation Material or "Cortoss") in comparison to two traditional polymethylmetharcrylate (PMMA) bone cement materials—PMMA1 (sold under the name Spineplex™- "Spineplex") and PMMA2 (sold under the tradename KyphX® HV-R "KyphX"), by measuring the contact angle of water on each material.

In addition, the contact angle of water on a second embodiment of the present invention material without fillers (e.g., a resin-only Cortoss sample without the filler materials) was measured to determine if the fillers affect wettability. Materials with contact angles (wetting angles)<90° are typically considered hydrophilic.

Testing was conducted by a contract laboratory-KSV Instruments.

Specimen Preparation: Rectangular test samples of each material were molded using the following process to produce the flat surface required for testing. Steel flexural test bar molds (13×5×100 mm) were cleaned with ethyl alcohol and air dried. Standard modeling putty was used to shorten the molds as the full length was not required, Glass microscope slides were placed on either side of the mold and taped down. The mold assembly was then clamped in place. Each type of material was prepared according to the manufacturer's instructions. The material of the present invention was mixed and expressed using static mixing tips. PMMA1 was mixed in a standard sterile specimen cup, drawn into a standard syringe and extruded into the mold. PMMA2 was mixed using the mechanical mixer, drawn into a standard syringe and extruded into the mold. The material was allowed to set in the mold for 24 hours at room temperature. Samples were then removed from the mold and stored in individual zip lock bags at ambient conditions prior to testing. For the resin-only testing, resin-only Cortoss was prepared by combining equal parts of A and B resin in a weigh boat and mixing thoroughly with a tongue depressor. The mixture was then poured onto a glass microscope slide. A second glass microscope slide was placed on top and the 2 slides were clamped together lightly.

Test equipment included a KSV Instruments CAM 101 with an environmental chamber to prevent evaporation for measurements exceeding 60 seconds and a Hamilton precision syringe.

Contact Angle Test Method: For droplet repeatability, gridlines were placed on the end of the needle tip and the droplet end. The droplet must have formed between these lines. Three (3) samples of each material were tested. Measurements were taken at 3 different locations on each sample. Short-term measurements were recorded between 10 seconds and 60 seconds after application of the droplet. One (1) sample of resin-only Cortoss was tested at 2 different locations.

Figure 3:
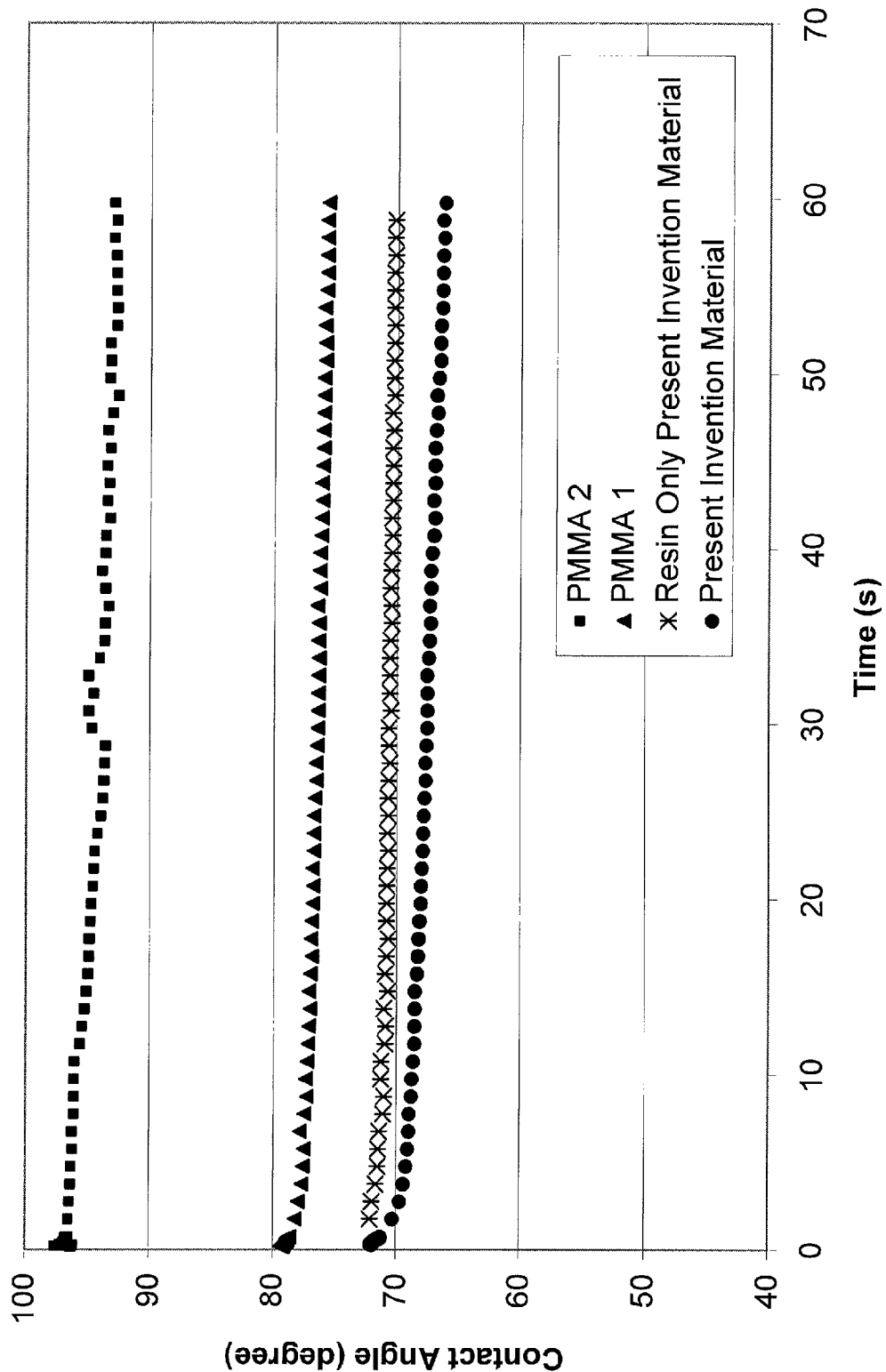
FIG. 3 demonstrates the hydrophilicity of the material utilized with the present invention via contact angle measurement in comparison to two traditional PMMA bone cement materials.
Figure 4:
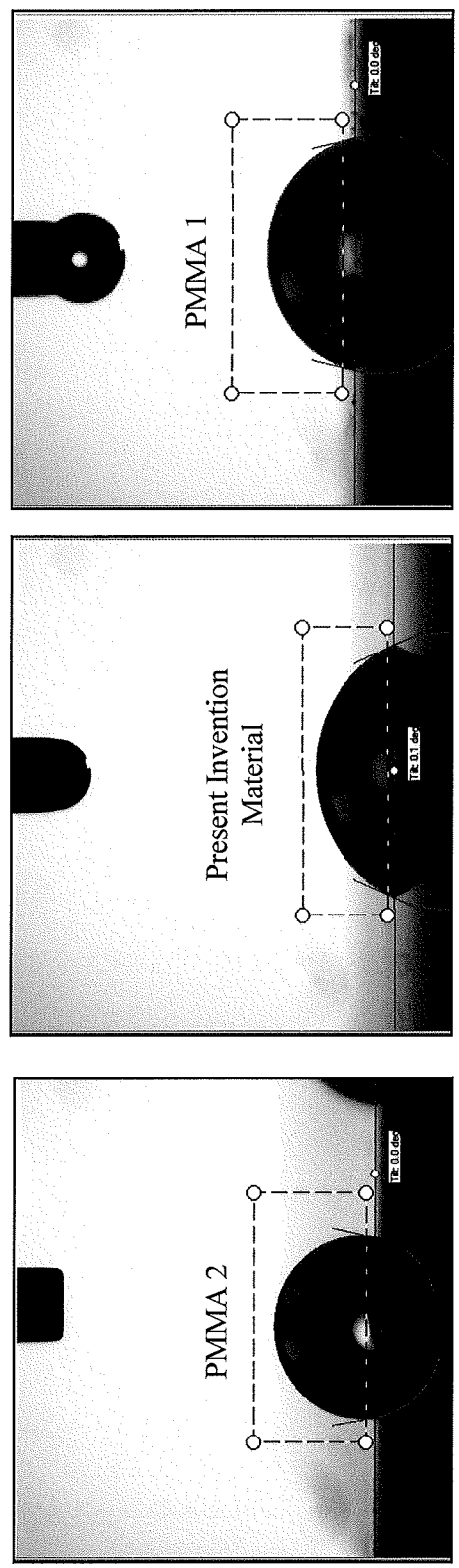
FIG. 4 depicts representative contact angle images of the material utilized with the present invention in comparison to two traditional PMMA bone cement materials.

Results; A summary of the average contact angle results can be found in Table 1. FIG. 3 shows contact angle versus time plots for a representative sample of each material. Representative images of the contact angle on the present invention material, PMMA 1 and PMMA 2 at 60 seconds can be seen in FIG. 4.

TABLE 1

Average contact angles over time for short-term measurements.

| Sample | Overall Average from short-term measurements (10 s-60 s) |
|---|---|
| Present Invention | 67.71° |
| PMMA1 | 75.86° |
| PMMA2 | 92.00° |
| Resin-Only Present Invention | 69.51° |

As disclosed herein, the materials employed in the present invention are more hydrophilic than traditional PMMA bone cement materials. The contact angle of water on the present invention material (with fillers) is similar to the contact angle of water on the same material without fillers ("resin-only") indicating that the fillers do not have an appreciable effect on the wettability of the present invention material.

Example

Pre-Clinical Evaluation of Present Invention Material in Ovine Vertebral Bodies

Three-level vertebral augmentations were performed in the lumbar vertebrae of six sheep. Two vertebrae per animal received the present invention material (Cortoss) and one vertebra per animal received traditional PMMA. Animals were sacrificed either at 3 months or 6 months. Outcome measures included computed tomography (CT) scans at the time of euthanasia, and histological evaluation.

Figure 5A:
FIGS. 5 and 5a are representative 3-month histological images after injection of the material of the present invention in the vertebrae of sheep spine.
Figure 5:
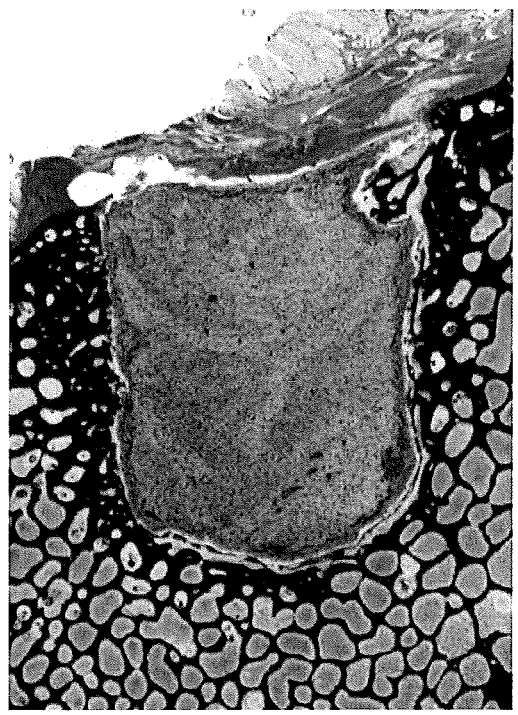
Figure 6A:
FIGS. 6 and 6a are representative 3-month histological images after injection of traditional PMMA bone cement material in the vertebrae of sheep spine.
Figure 6:
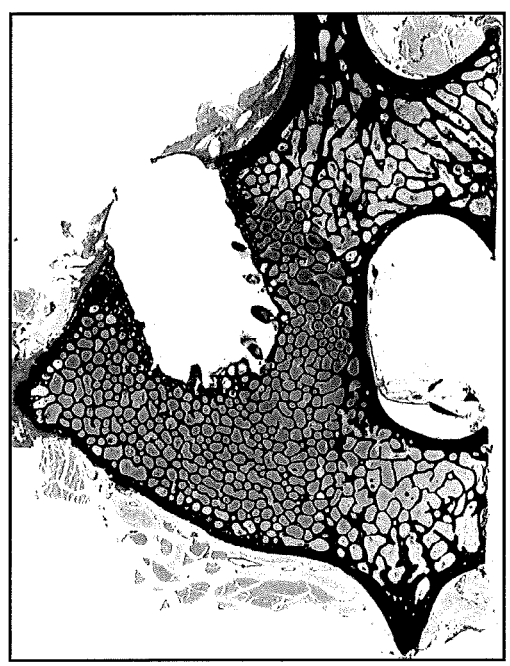
Figure 7A:
FIGS. 7 and 7a are representative 6-month histological images after injection of the material of the present invention in the vertebrae of sheep spine.
Figure 7:
Figure 8A:
FIGS. 8 and 8a are representative 6-month histological images after injection of traditional PMMA bone cement material in the vertebrae of sheep spine.
Figure 8:

All sheep were housed at Colorado State University (CSU) facilities. All surgical procedures were conducted utilizing routine aseptic techniques. In brief, for each of the animals, the lumbar region was prepared for surgery and the animal was placed right laterally recumbent on the table. The area was cleansed and draped. A lateral retroperitoneal approach was made through the oblique abdominal muscles to the plane ventral to the transverse processes. The lateral sides of the L3, L4 and L5 vertebral bodies were exposed. A drill bit was used to create 8 mm diameter holes in each of the three vertebral bodies. After using a curette to remove a small amount of bone from each of the holes, the defects were filled with either the present invention test material or PMMA control material. The muscle layers were then re-approximated using absorbable sutures; the subcutaneous tissue was apposed with absorbable sutures; and the skin was re-approximated with non-resorbable sutures in a Ford interlocking pattern. Post-operative monitoring included inspection of the surgical site and return to normal physiological function. Upon sacrifice, each lumbar region was explanted and transported to Cleveland Clinic Foundation (CCF) for histological evaluation. Representative 3 and 6-month histological images of the implanted materials are shown in FIGS. 5 and 5a (present invention 3-month images), FIGS. 6 and 6a (PMMA 3-month images), FIGS. 7 and 7a (present invention 6-month images) and FIGS. 8 and 8a (PMMA 6-month images).

Under the conditions of this study, the material of the present invention performed suitable as a bone augmentation material in sheep drill-hole defects. In the 3-month present invention samples, focal bone apposition was noted. By 6-months, viable bone formed along the periosteal surface of the present invention defect sites. The present invention material was noted to flow and interdigitate into the bone beyond the defect site without disturbing the adjacent bone, to a greater degree than the PMMA material.

Example

Clinical Evaluation of Present Invention Material in Vertebroplasty Procedures

Materials and Methods: A clinical study, which was conducted under an Investigational Device Exemption (IDE) granted by the Food and Drug Administration (FDA), evaluated the safety and effectiveness of the present invention material (Cortoss) as compared to PMMA bone cement (PMMA1-Spineplex) in vertebral augmentation using the vertebroplasty technique. This study was conducted at 21 sites in the United States over a three-year period beginning February 2004 and ending February 2007. Two hundred and fifty-six (256) patients suffering from pain associated with osteoporosis-induced vertebral compression fractures (VCFs) (Cortoss, n=162; PMMA1, n=94) were enrolled in the prospective, randomized, controlled clinical trial.

The majority of patients in both the Cortoss (124 patients) and PMMA1 control (75 patients) groups underwent single-level procedures. Of the remaining 57 patients, all but two underwent two-level procedures—one Cortoss and one control patient were treated at three levels.

On average, 51.7% more material was used for each level treated with PMMA (3.49 cc) when compared to Cortoss (2.30 cc). The Cortoss was delivered using a co-axial catheter method that is part of the Aliquot™ Delivery System. No specific delivery system requirements were in place for PMMA cases; investigators used their system of choice. The majority of patients in both groups (64.2% Cortoss, 67.0% control) were treated under local anesthesia with conscious sedation.

Surgical characteristics were similar between the two groups, with a mean procedure duration of 30.8 minutes for the Cortoss group and 30.7 minutes for the control group for single-level treatment; the average duration for two or more levels was 43.7 minutes in both groups.

Outcome Measures: A primary composite endpoint was used to assess clinical outcomes. The primary efficacy measures and their definitions of success were as follows: (1) Pain: an improvement of at least 20 points on the Visual Analogue Pain Scale (VAS) and an overall VAS score of no more than 50 on a 100-point scale, (2) Function: maintenance or improvement in Oswestry Disability Index (ODI), (3) Stability: maintenance of vertebral height and alignment (an independent radiologist blinded to treatment assignment developed and applied a consistent method for analyzing vertebral height and alignment), and (4) Safety: no device-related subsequent surgical interventions at the study treated level.

Patient Demographics: Patient demographics of the two study groups were similar, except that at study entry a larger proportion of the Cortoss group had respiratory comorbidities (39.5% Cortoss vs. 24.5% PMMA1 control), and more PMMA patients had nervous system comorbidities than Cortoss patients (16.0% Cortoss group vs. 36.2% PMMA1 control). The median age of the patients in both groups was 78. The mean height and weight were also similar (approximately 65 inches and 152 lbs.). Also well matched was gender, with 71.6% females in the Cortoss group and 77.7% females in the control group.

Patients entered the study reporting a duration of pain that ranged from less than six weeks to greater than one year. The majority of the patients in both groups (48.8% Cortoss, 53.8% control) entered the study with between 6 and 12 weeks of back pain, and most experienced an increase of daytime bed rest of between 2 and 4 hours. As would be expected in an elderly population with osteoporosis, 99.2% of patients entered the study with multiple comorbidities, including respiratory, nervous system, cardiovascular, urinary, gastrointestinal, reproductive, skin, endocrine, immunological, psychological, EENT (eyes, ears, nose, throat-systems review), head and neck, and other conditions. Nearly 80% had cardiovascular co-morbidities, and 76.6% had spinal co-morbidities, which could have a significant impact on clinical evaluations using VAS and ODI measures.

Initial VAS and ODI function scores were comparable in the two groups. The VAS baseline score averaged 80 in the Cortoss group and 78 in the control group. The average baseline ODI score was 60 in both groups.

In accordance with the pre-defined statistical analysis plan for this study, non-inferiority was determined at the 24-month time point using the primary composite endpoint. To be considered a success for the composite endpoint, patients were required to be a success for every primary safety and efficacy measurement (pain, function, maintenance of height and alignment, and no subsequent intervention). The results confirm the hypothesis that Cortoss is non-inferior to PMMA in the vertebral augmentation procedures for VCFs at a confidence interval of 95%, and a δ of 10%. The individual outcome measures and the results at other follow-up time points are shown in Table 2.

TABLE 2

Individual Component and Combined Endpoints and at 3 and 24 Months

|  | Present Invention Material (Cortoss) | | Traditional PMMA Material (PMMA 1) | |
| --- | --- | --- | --- | --- |
|  | 3-Month | 24-Month | 3-Month | 24-Month |
| Improvement in VAS Score | 116/134 (86.6%)[1] | 101/123 (82.1%) | 57/76 (75.0%)[1] | 54/69 (78.3%) |

TABLE 2-continued

Individual Component and Combined Endpoints and at 3 and 24 Months

|  | Present Invention Material (Cortoss) | | Traditional PMMA Material (PMMA 1) | |
| --- | --- | --- | --- | --- |
|  | 3-Month | 24-Month | 3-Month | 24-Month |
| (≥20 mm improvement + VAS score ≤50 mm) | | | | |
| Maintenance or Improvement in ODI Score | 127/134 (94.8%) | 119/123 (96.7%)[1] | 75/76 (98.7%) | 61/69 (88.4%)[1] |
| Maintenance of Vertebral Height and Alignment | 132/133 (99.2%) | 113/115 (98.3%) | 76/76 (100.0%) | 63/63 (100.0%) |
| No Subsequent Device-Related Surgical Intervention at Index treatment level(s) | 135/137 (98.5%) | 122/124 (98.4%) | 77/77 (100.0%) | 70/70 (100.0%) |
| Combined Treatment Success 24 Months[1] | 111/134 (82.8%) | 90/117 (76.9%) | 56/76 (73.7%) | 47/64 (73.4%) |

[1]Significant difference Cortoss over PMMA at p < 0.05, Fischer Exact Test

Figure 9:
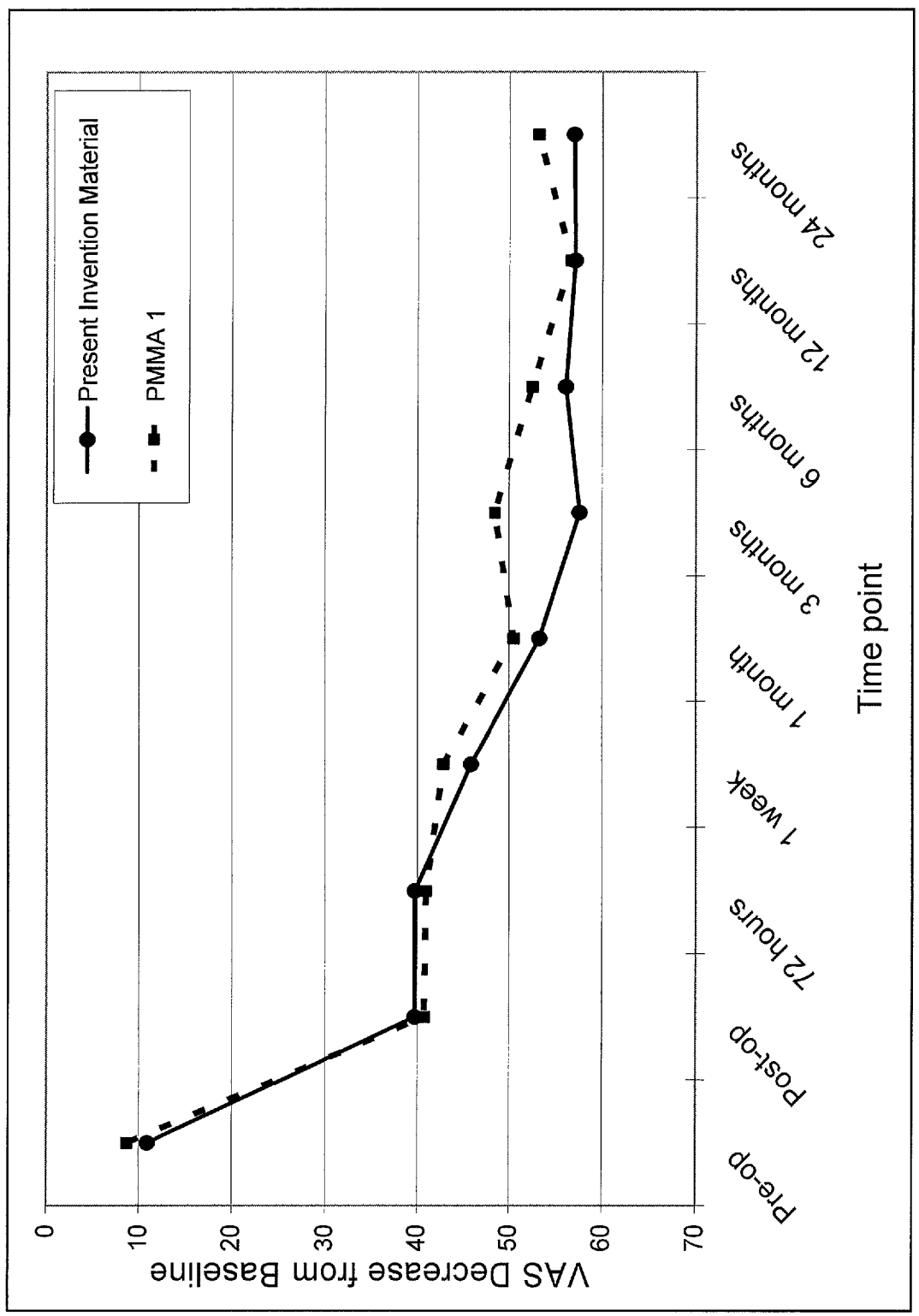
FIG. 9 is a graphical depiction of the measured decrease in pain (measured using the Visual Analogue Pain Scale (VAS)) in a patient population treated utilizing the present invention material and traditional PMMA material. The data demonstrate that the present invention consistently provided equal or better pain relief, particularly at 3 months, compared to treatment with traditional PMMA material.

With regard to individual endpoints, a statistically significantly greater percentage of Cortoss patients (86.6%) than PMMA patients (75.0%) were a success for pain at 3 months, a difference of 11.6% (p<0.05). The same is true for function at 24 months, when 96.7% of Cortoss patients met the definition of success as opposed to 88.4% of PMMA patients, a difference of 8.3% (p<0.05). At these time points the average improvements in VAS and ODI also were significantly greater. The difference in function results at 24 months was further confirmed by a significant difference (p<0.05) in the physical functioning ability as measured by the SF-12. FIG. 9 shows the average decrease in pain from baseline for both groups, demonstrating that Cortoss consistently provides equal or better (3 months) pain relief compared to PMMA.

Figure 10:
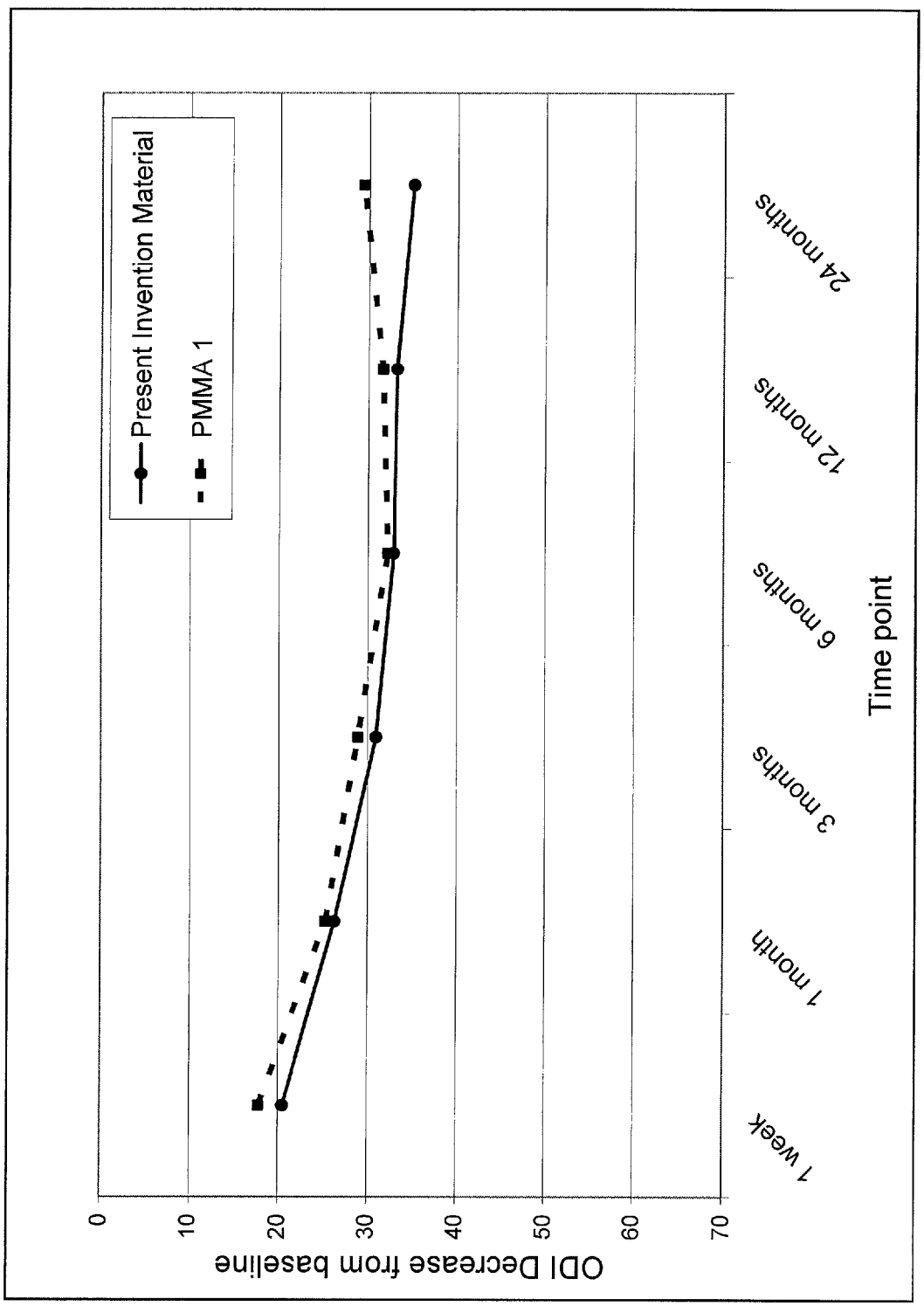
FIG. 10 is a graphical depiction of both materials' (present invention material and traditional PMMA material) effect on patients' functioning as measured using the Oswestry Disability Index (ODI). The data demonstrate that the present invention consistently provided equal or better (24 months) preservation or improvement in functioning compared to treatment with traditional PMMA.

FIG. 10 depicts both materials' effect on patients' functioning. The values are the average decrease in disability, or improvement in functioning, at each time point. Maintenance of vertebral height and alignment in each group was closely matched at all assessment intervals. On the basis of subsequent surgical interventions, two of the 162 Cortoss patients were considered a failure by requiring surgery at the treated site. One of these was for intercostal neuritis and one for further fracture. Both were treated successfully, the latter with Cortoss.

Pain medication usage dropped steadily and significantly for both groups over time, with 90.7% of Cortoss patients and 86.2% of the PMMA using an analgesic at baseline and declining to 44.1% of Cortoss patients and 40.0% of PMMA patients at the 24-month evaluation.

Physician ease-of-use ratings of both materials was high, with a higher proportion of physicians—63%—rating Cortoss as "very easy" compared to 54% who gave PMMA that same designation.

The incidence of serious adverse events that were reported as possibly related to the procedure or device-related was low in both groups—4.3% in each. These events included new fractures, muscle spasm, hypertension, and redness at the incision site.

Example

Analysis of Fracture-Free Population

In the previous Example, new fractures at any level occurred more in patients treated with PMMA than those treated with the present invention material—31.9% vs. 27.8% of patients, respectively. Studies have shown that the presence of multiple existing VCFs at baseline substantially increases the risk of developing a new VCF (Lindsay R, et al. *Risk of new vertebral fracture in the year following a fracture*, JAMA, 2001, 285: 320-323; Voormolen M H J, et al. *The risk of new osteoporotic vertebral compression fractures in the year after percutaneous vertebroplasty*, J Vasc Interv Radiol, 2006, 17: 71-76).

Therefore, a sub-population of patients from the above Example was further evaluated. Specifically, patients treated utilizing the present invention material (Cortoss) and treated utilizing PMMA, who had not had a previous vertebral body compression fracture prior to study enrollment, were further evaluated. Patients with no previous fracture at study outset and with only one level treated comprised a "virgin back" subset of patients, which provided a more homogeneous basis for comparison of the two treatments. In this study there were 112 "virgin back" patients. In this group, 27.3% of the PMMA patients developed a new fracture while for Cortoss patients the rate was 17.6%. This represents a decreased incidence of 35% for the Cortoss group versus the PMMA group. In these patients the incidence of fractures at an adjacent level was also higher in the PMMA group—18.2%—than in the Cortoss group—10.3%—representing a decreased incidence of 43% in Cortoss patients (Table 3).

TABLE 3

Summary of New Fractures in Patients That Only Had One Previous Vertebroplasty Procedure

| Treatment | No. (%) of Patients with a New Fracture(s) (adjacent, non-adjacent, treatment level) | No. (%) of Patients with a Subsequent Fracture(s) that Resulted In Hospitalization | No. (%) of Patients with a Subsequent Fracture(s) that Required Surgical Intervention (Vertebroplasty, Kyphoplasty) |
|---|---|---|---|
| Present Invention Material (Cortoss) | 12 (17.6%) | 2 (2.9%) | 5 (7.4%) |
| PMMA1 | 12 (27.3%) | 5 (11.4%) | 10 (22.7%) |

Example

Correlation of Fill Volume to Subsequent Fracture Rates

To assess the effect of fill volume on the rate of subsequent fracture, a sub-set of osteoporotic patients treated under the FDA IDE study described in the Example above were evaluated. In the original study, patients with VCF's at one or two levels were included. In order to perform a logistic regression analysis on the potential effect of fill volume on subsequent new fracture rate, it was necessary to stratify and include only the subset of study patients who, at the index procedure, had a single-level vertebral compression fracture treated.

Methods: Of the 256 osteoporotic VCF patients enrolled in the prospective randomized IDE study (162 treated utilizing the material described in the present invention and 94 treated with PMMA), 199 were treated at a single level (122 in the present invention group "Cortoss" and 75 in the PMMA group). These 199 patients constitute the sub-set analyzed.

Results: In this subset, the mean fill volumes were 2.36 cc and 3.70 cc respectively for Cortoss and PMMA; and the subsequent fracture rates were 29/124 Cortoss (23.4%) and 22/75 PMMA (29.3%). The logistic regression results are presented in Table 4.

TABLE 4

| Treatment Group | Fracture Rate | Mean Fill Volume (cc) | Slope Estimate | SE | Odds Ratio | p-value |
|---|---|---|---|---|---|---|
| Cortoss | 29/124 (23.4%) | 2.36 | 0.0485 | 0.1616 | 1.05 | 0.7638 |
| PMMA | 22/75 (29.3%) | 3.70 | 0.1929 | 0.1120 | 1.21 | 0.0850 |

For Cortoss, the high p-value (i.e., 0.76380), combined with the odds ratio close to 1 (i.e., 1.05), demonstrates that the fill volume of Cortoss has little effect on the incidence of new fracture (e.g., the occurrence of new fractures is minimized by the diffuse fill pattern of the material). For PMMA, the p-value of 0.085 suggests a strong trend that higher fill volumes of PMMA are associated with an increased risk of subsequent new fractures. The odds ratio of 1.21 indicates that each additional 1 cc of PMMA is associated with a 21% increase in the odds of a new fracture. This analysis of prospective clinical data demonstrates that vertebral augmentation using a large volume of PMMA can alter the biomechanics of the spine and thereby increase the risk of new fracture.

This analysis provides clinical evidence that the more physiologic distribution pattern seen with the material of the present invention may offer biomechanical advantages over the bolus fill of PMMA and explain the lower rate of subsequent fractures in single-level VCF patients treated in the FDA IDE study described in the Example above using the material of the present invention.

Example

Initial Compressive Strength of Present Invention

In addition to the features described throughout, another feature of the present invention material that may enhance its performance in vertebral augmentation is the ability of the material to bear load within short time intervals. In order to quantify this property, the compressive strength of the present invention material (Cortoss) was compared to PMMA3 (sold under the tradename Simplex P) as a function of curing time at 37° C. Samples were prepared in accordance with the respective manufacturer's instructions as well as ASTM F 451 "Standard Specification for Acrylic Bone Cement" Section 7.9 (Compressive Strength) and ISO 5833 "Implants for Surgery-Acrylic Resin Cements Annex E (Method for Determination of Compressive of Cement). A summary of the results is provided below. Data demonstrate that Cortoss has a higher maximum compressive strength than Simplex P under any circumstances, and is 100% stronger at 15 minutes post-mix than Simplex P after 24 hours. Cortoss also has a 32% higher yield stress at 15 minutes than Simplex P at 24 hours. Comparing the 15-minute time points, Cortoss is 100% higher at the yield stress and 400% higher at the maximum compressive stress. Moreover, Cortoss reaches 72% of its full (maximum) strength by 15 minutes while Simplex P reaches only 45.5%.

Table 5 summarizes the compressive test data for Cortoss and PMMA3 (Simplex P) as a function of time.

TABLE 5

| Time Post Mixing | CORTOSS Yield Stress (MPa) | Percent of Maximum | CORTOSS Maximum Stress (MPa) | Percent of Maximum |
|---|---|---|---|---|
| 15 min | 61.45 | 31.9% | 160.45 | 72.4% |
| 90 min | 86.05 | 44.7% | 186.32 | 84.0% |
| 4 hrs | 96.67 | 50.2% | 193.83 | 87.4% |
| 24 hrs | 192.48 | 100.0% | 221.68 | 100.0% |

| Time Post Mixing | PMMA Yield Stress (MPa) | Percent of Maximum | PMMA Maximum Stress (MPa) | Percent of Maximum |
|---|---|---|---|---|
| 15 min | 30.83 | 51.2% | 40.1 | 45.5% |
| 90 min | 35.22 | 58.5% | 54.37 | 61.7% |
| 4 hrs | 39.06 | 64.9% | 60 | 68.1% |
| 24 hrs | 46.47 | 77.2% | 75.15 | 85.3% |

Example

Viscosity and Injectability of Present Invention

The therapeutic properties of the present invention are due, in part, to the constant and relatively low viscosity and injection pressure of the polymer composite. Material viscosity is proportional to the force required to extrude the material through a constant orifice. During polymerization, most materials exhibit an increase in viscosity before setting occurs. The following test procedure was carried out to measure the force required to extrude viscosity standards through a 10 cc syringe with a standard male luer aperture. The correlation between extrusion force and viscosity was then used to characterize the viscosity of the present invention material (Cortoss) and PMMA as they polymerize over time.

Cannon viscosity standards N30000, N62000, N150000, and N190000, N450000 and N2700000 were filled into 10 mL BD syringes. The syringes were inverted to allow for any air bubbles to rise to the Luer of the syringe (up to 24 hours for the high viscosity standards). Air pockets were expelled prior to testing. Using a mix-tip with Luer lock attachment, Cortoss was front filled into a 10 mL BD syringe using a 3-way stopcock. Extrusion force testing was initiated within about 1 minute of filling the BD syringe. PMMA1 (Spineplex) was prepared according to the manufacturer's instructions by mixing the powder and liquid components by hand. The Spineplex was aspirated into a 10 ml. BD syringe. Testing was initiated within 2 minutes of the start of mixing.

An Instron model 4467 with a 1 kN load cell was used for testing, with a constant cross head speed of 4.1 mm per minute. This translates to approximately 0.67 cc per minute, or 10 cc per 15 minutes, which is approximately the duration of the curing profile for PMMA. Plots of extrusion force versus time for each sample were output by the Bluehill software.

The cannon viscosity standards produced relatively constant extrusion force profiles over the course of the experiment. The steady state extrusion force for each standard was plotted versus viscosity to develop a correlation between extrusion force and viscosity. Table 6 lists the steady state extrusion force range of data for each viscosity standard. The data were plotted in Microsoft Excel and an automatic trendline was generated to define the correlation, using the "Power" trendline function. The relationship between extrusion force through a luer aperture of a 10 cc syringe and viscosity is: Viscosity=13170*(Extrusion Force)^1.2142, with a correlation coefficient of $R^2$=0.9904.

TABLE 6

Steady State Extrusion Force for Viscosity Standards

| Standard | Viscosity cP | Steady State Extrusion Force | | |
|---|---|---|---|---|
| | | Low N | High N | Mean N |
| N30000 (P/N 9727-E25): | 80,000 | 4 | 6 | 5 |
| N62000 (P/N 9727-E27): | 200,000 | 7.5 | 9.5 | 8 |
| N150000 (P/N 9727-E29): | 420,000 | 13 | 16.5 | 16 |
| N190000 (P/N 9727-E30): | 520,000 | 21 | 23 | 22 |
| N450000 (P/N 9727-E35): | 1,600,000 | 57 | 60 | 59 |
| N2700000 (P/N 9727-E40): | 5,300,000 | 121 | 135 | 130 |

Figure 11:
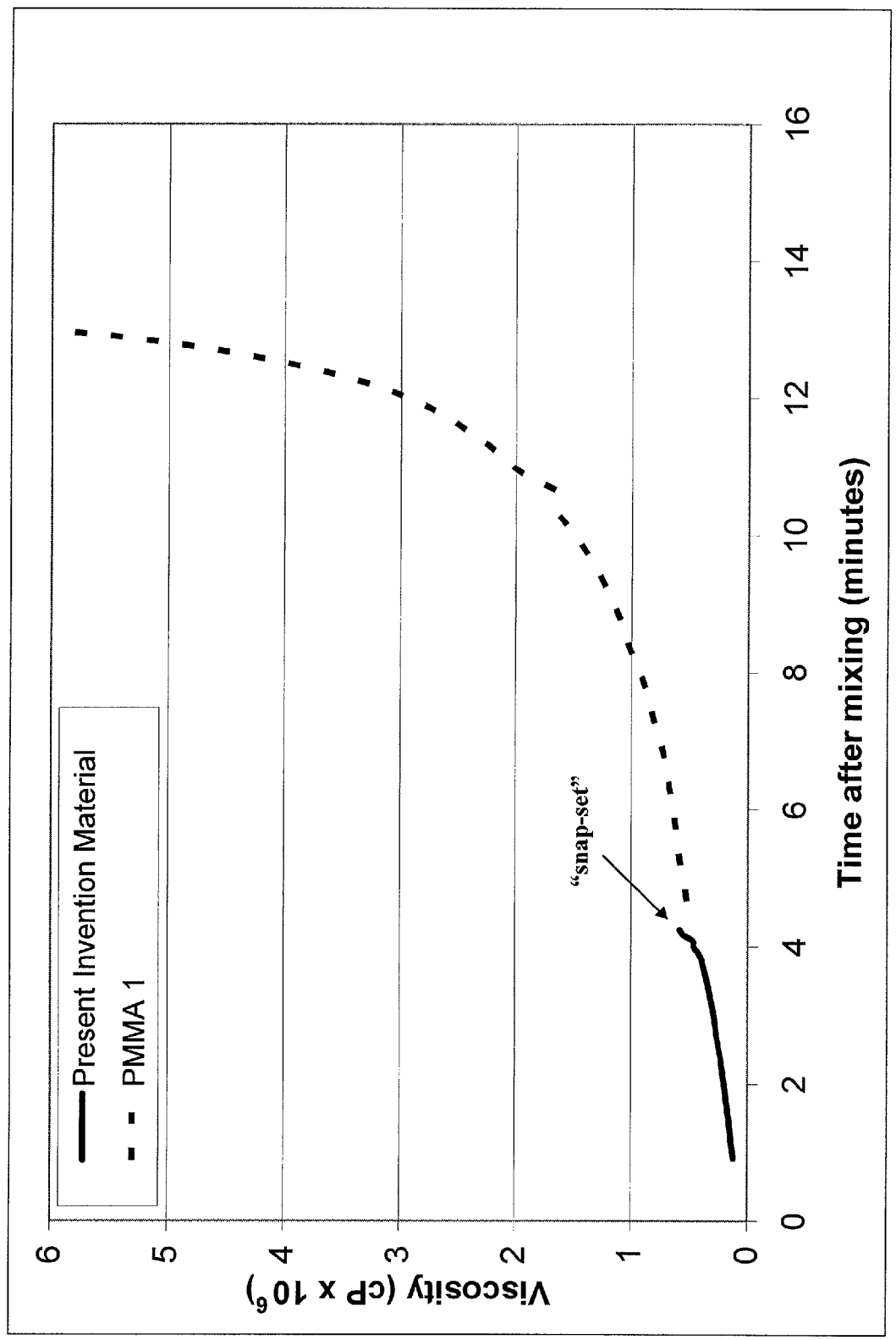
FIG. 11 displays the change in viscosity for the present invention material and PMMA during material working time.

The correlation function for transforming extrusion force into viscosity was applied to the data for Cortoss and Spineplex. FIG. 11 displays the change in viscosity for Cortoss and Spineplex during material working time. Cortoss exhibited a relatively consistent extrusion profile corresponding to constant viscosities from about 100,000 cP to about 300,000 cP before the material cured/hardened. A rapid increase in the measured extrusion force is observed at about 4.5 minutes (250-280 seconds) after mixing, corresponding to the "snap-set" (i.e., hardening within 30 seconds) of Cortoss. Spineplex PMMA exhibited a gradually increasing viscosity, representing a gradual but significant thickening prior to final solidification/hardening. The initial extrusion forces ranged from 200,000 to 400,000 cP in the time periods immediately following mixing and prior to the start of the material's working time. The viscosity continued to increase to approximately 3,000,000 cP (approximately ten-fold) prior to curing at about 11 minutes (650-700 seconds) after mixing.

These data demonstrate that Cortoss exhibits a relatively constant extrusion force and viscosity profile after mixing prior to rapidly "snap-setting". Spineplex does not exhibit a "snap" set. Instead, Spineplex gradually increases in viscosity prior to curing.

To measure injection pressure, Cortoss, PMMA1 (Spineplex), and PMMA2 (KyphX HV-R) were prepared according to the manufacturer's instructions for use. After mixing, the materials were filled into a 1 cc syringe and 6" catheter assembly (Aliquot Delivery System, Orthovita, Inc.). The force required to extrude the material over the course of its working time was measured on an Instron Mechanical Test Frame with a custom fixture, using a fixed displacement rate of 1 mm/min.

Figure 12:
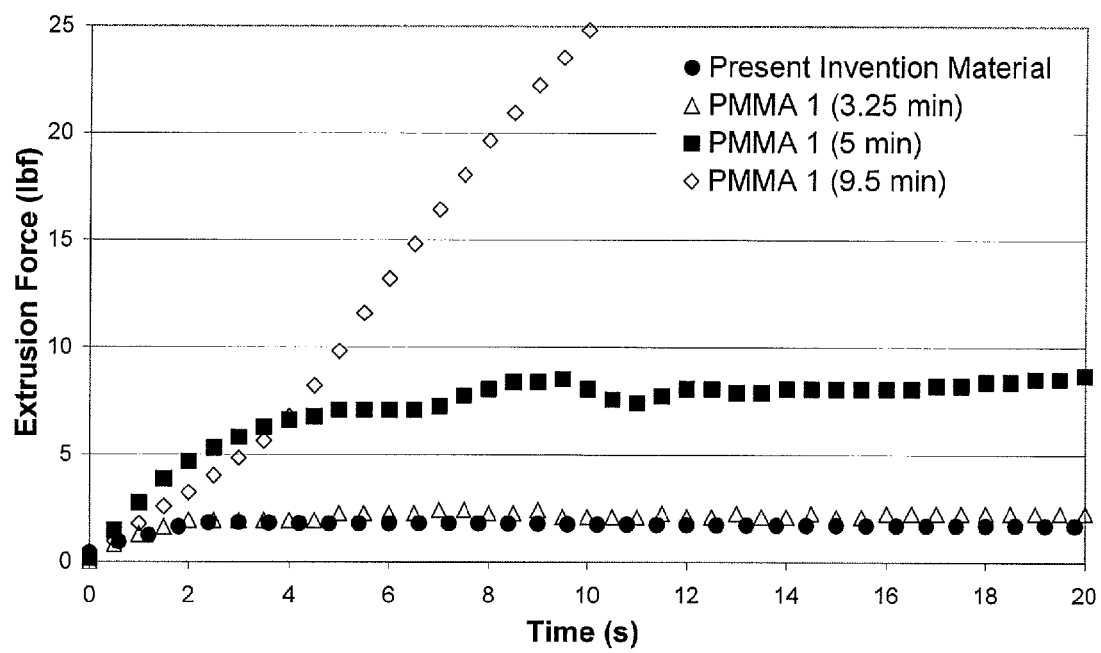
FIG. 12 demonstrates the maximum extrusion force for the present invention material as compared to two traditional PMMA bone cement materials during material working time. The materials were extruded through a 1 cc syringe and 6 inch catheter assembly.
Figure 12:
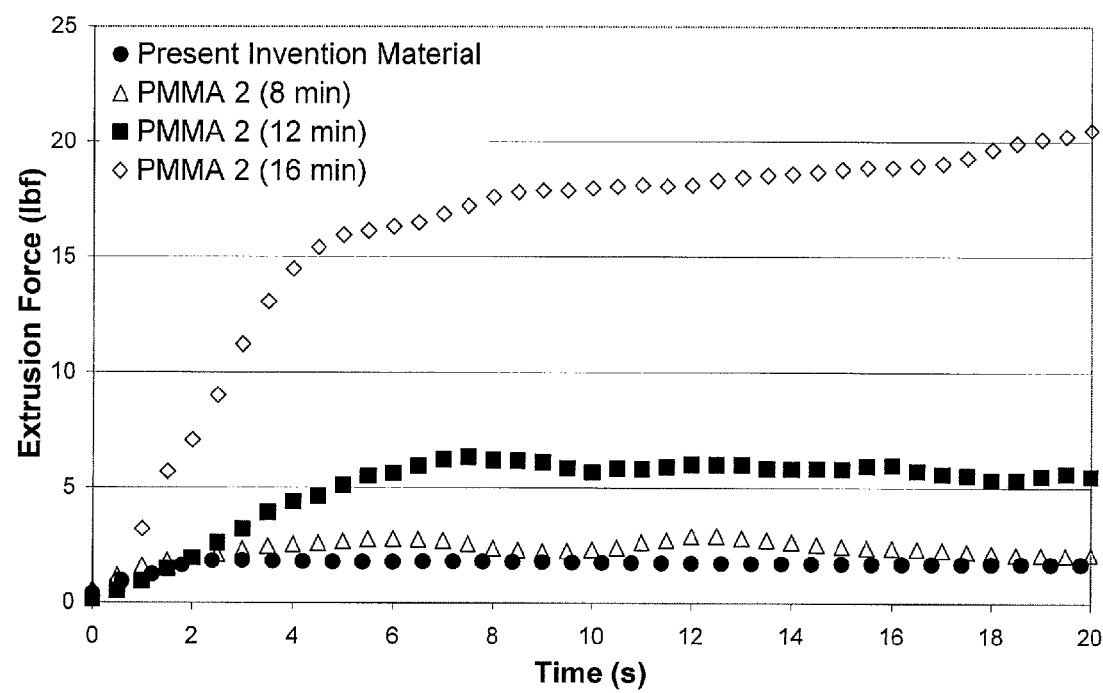

FIG. 12 demonstrates the maximum extrusion force for Cortoss as compared to the two PMMA cements. Cortoss is ready to be injected immediately after mixing, and maintains a constant viscosity (i.e., a viscosity that does not rapidly change more than five-fold over time); and extrusion force of approximately 1.7 lbf until the material sets/hardens. The working phase of KyphX is approximately 8 to 16 minutes post-mixing. During this time the viscosity increases (i.e., the viscosity of the material rapidly changes over time with a ten-fold or greater increase in absolute viscosity as the material increasingly thickens through a dough state prior to hardening) and the extrusion force ranges from approximately 1.6 to 20 lbf. The working phase of Spineplex is approximately 2 to 15 minutes post-mixing. During this time the viscosity increases and the extrusion force ranges from approximately 2.5 to 60 lbf.

The increasing viscosity of KyphX and Spineplex requires increasingly higher injection pressures over each material's working time. This ranges from 1.6 to greater than 20 lbf for Kyphx and 2.5 to greater than 60 lbf for Spineplex. The variable, increasing viscosity of these PMMA cements leads to a dense bolus of material which displaces the natural cancellous network of the vertebra. The consistent viscosity of Cortoss provides for ease of injectability at an injection pressure of approximately 1.7 lbf. This allows Cortoss to flow evenly within the blood and marrow filled vertebral body, coating and reinforcing the existing trabecular architecture in a physiologic manner, which also results in lower fill volumes required during clinical use.

The disclosures of each and every patent, patent application, and publication cited herein are hereby incorporated herein by reference in their entirety. Although the present invention has been described with reference to restorative biomaterials, it should be understood that aspects of the present invention, such as the sterile compositions themselves, the sterilization methods of the constituents that comprise the compositions, and their methods of use for a restorative bone composition, are not limited to the particular embodiments disclosed. While the present invention has been particularly shown and described with reference to the presently preferred embodiments thereof, it is understood that the invention is not limited to the embodiments specifically disclosed herein. Numerous changes and modifications may be made to the preferred embodiment of the invention, and such changes and modifications may be made without departing from the spirit of the invention. It is therefore intended that the appended claims cover all such equivalent variations as they fall within the true spirit and scope of the invention.

What is claimed is:

1. A method for reducing the occurrence of new post-operative fractures in adjacent vertebrae of a human patient's spine after a vertebroplasty procedure performed to stabilize a fracture in a vertebra of a patient, the method comprising the steps of:
    performing a vertebroplasty procedure to stabilize a fracture in a vertebra of the patient, wherein the vertebroplasty procedure comprises the step of injecting a material into the fractured vertebra in an amount less than 3 cc;
    wherein the material is formed by mixing together a first paste and a second paste;
    wherein the first paste comprises bisphenol-A-glycidyl dimethacrylate (bis-GMA), triethylene glycol dimethacrylate (TEGDMA), silica, and bioactive glass;
    wherein the second paste comprises bisphenol-A-glycidyl dimethacrylate (bis-GMA), triethylene glycol dimethacrylate (TEGDMA), bisphenoi-A-ethoxy dimethacrylate (bis-EMA), barium-boroaluminosilicate glass, and silica;
    wherein the material has a constant viscosity from about 100,000 to about 400,000 cP for allowing the material to flow and interdigitate into a structure of the vertebra; and
    wherein the method reduces the occurrences of new post-operative fractures.

2. The method of claim 1 wherein the first paste further comprises a polymerization initiator.

3. The method of claim 1 wherein the second paste further comprises a polymerization initiator.

4. The method of claim 1 wherein the filler further comprises a coupling agent.

5. A method for reducing the risk of new post-operative fractures in a human patient's adjacent vertebrae after a vertebroplasty procedure to stabilize a fracture in a vertebra of the patient, the method comprising the steps of:
    performing a vertebroplasty procedure to stabilize a fracture in a vertebra of the patient;
    wherein the vertebroplasty procedure comprises the step of injecting a material into the fractured vertebra in an amount less than 3 cc;
    wherein the material is formed by mixing together a first paste and a second paste;
    wherein the first paste comprises bisphenol-A-glycidyl dimethacrylate (bis-GMA), triethylene glycol dimethacrylate (TEGDMA), silica, and bioactive glass;
    wherein the second paste comprises bisphenol-A-glycidyl dimethacrylate (bis-GMA), triethylene glycol dimethacrylate (TEGDMA), bisphenoi-A-ethoxy dimethacrylate (bis-EMA), barium-boroaluminosilicate glass, and silica;
    wherein the material has a constant viscosity from about 100,000 to about 400,000 cP for allowing the material to flow and interdigitate into a structure of the vertebra, and
    wherein the method reduces the risk of new post-operative fractures in the adjacent vertebrae.

6. The method of claim 5 wherein the material is hydrophilic and has a contact angle less than 75 degrees.

7. A method for reducing the risk of fractures in a human patient's adjacent vertebrae and to alleviate pain after a vertebroplasty procedure performed to stabilize a fracture in a vertebra of the patient, the method comprising the steps of:
    performing a vertebroplasty procedure to stabilize a fracture in a vertebra of the patient, wherein the vertebroplasty procedure comprises the step of injecting a material into the fractured vertebra in an amount less than 3 cc, and allowing the material to harden for a period of 2.0-8.0 minutes to obtain heightened pain relief at about 3 months after the step of performing the vertebroplasty procedure; wherein the material is formed by mixing together a first paste and a second paste,
    wherein the first paste comprises bisphenol-A-glycidyl dimethacrylate (bis-GMA), triethylene glycol dimethacrylate (TEGDMA), silica, and bioactive glass;
    wherein the second paste comprises bisphenol-A-glycidyl dimethacrylate (bis-GMA), triethylene glycol dimethacrylate (TEGDMA), bisphenoi-A-ethoxy dimethacrylate (bis-EMA), barium-boroaluminosilicate glass, and silica;
    wherein the material has a constant viscosity from about 100,000 to about 400,000 cP for allowing the material to flow and interdigitate into a structure of the vertebra; and
    wherein the method reduces the risk of fractures in the adjacent vertebrae.

8. A method for reducing the risk of fractures in a human patient's adjacent vertebrae and to preserve physical functioning of the patient after a vertebroplasty procedure performed to stabilize a fracture in a vertebra of the patient, the method comprising the steps of:
    performing a vertebroplasty procedure to stabilize a fracture in a vertebra of the patient, wherein the vertebroplasty procedure comprises the step of injecting a material into the fractured vertebra in an amount less than 3 cc, and allowing the material to harden for a period of 2.0-8.0 minutes to obtain better preservation of physical functioning of the patient at about 24 months after the step of injecting the material;
    wherein the material is formed by mixing together a first paste and a second pastes;

wherein the first paste comprises bisphenol-A-glycidyl dimethacrylate (bis-GMA), triethylene glycol dimethacrylate (TEGDMA), silica, and bioactive glass;

wherein the second paste comprises bisphenol-A-glycidyl dimethacrylate (bis-GMA), triethylene glycol dimethacrylate (TEGDMA), bisphenoi-A-ethoxy dimethacrylate (bis-EMA), barium-boroaluminosilicate glass, and silica;

wherein the material has a constant viscosity from about 100,000 to about 400,000 cP for allowing the material to flow and interdigitate into a structure of the vertebra; and wherein the method reduces the risk fractures in the adjacent vertebrae.

9. A method for reducing the risk of fractures in a human patient's adjacent vertebrae and simultaneously reducing the patient's exposure to implant material after a vertebroplasty procedure performed to stabilize a fracture in a vertebra of the patient, the method comprising the steps of:

performing a vertebroplasty procedure to stabilize a fracture in a vertebra of the patient, wherein the vertebroplasty procedure comprises the step of injecting a material into the fractured vertebra in an amount less than 3 cc, and allowing the material to harden for a period of 2.0-8.0 minutes;

wherein the material is formed by mixing together a first paste and a second paste to produce the material;

wherein the first paste comprises bisphenol-A-glycidyl dimethacrylate (bis-GMA), triethylene glycol dimethacrylate (TEGDMA), silica, and bioactive glass;

wherein the second paste comprises bisphenol-A-glycidyl dimethacrylate (bis-GMA), triethylene glycol dimethacrylate (TEGDMA), bisphenoi-A-ethoxy dimethacrylate (bis-EMA), barium-boroaluminosilicate glass, and silica;

wherein the material has a constant viscosity from about 100,000 to about 400,000 cP for allowing the material to flow and interdigitate into a structure of the vertebra;

wherein the viscosity and flow characteristics of the material provide adequate fill of a given vertebral body volume and limit the volume of material leakage outside of the vertebral body thereby reducing the patient's exposure to implant material; and wherein the method reduces the risk of fractures in the adjacent vertebrae.

* * * * *